United States Patent [19]

Kornguth et al.

[11] Patent Number: 5,629,213

[45] Date of Patent: May 13, 1997

[54] ANALYTICAL BIOSENSOR

[76] Inventors: Steven E. Kornguth, 1114 Shorewood Blvd., Madison, Wis. 53705; Robert M. Corn, 4018 Manitou Way, Madison, Wis. 53711; Claire E. Jordan, 707 W. Main St., Madison, Wis. 53715; Brian L. Frey, 526 Spruce St., Madison, Wis. 53715

[21] Appl. No.: 398,470

[22] Filed: Mar. 3, 1995

[51] Int. Cl.$^6$ .............. G01N 33/543; G01N 33/552; G01N 33/547

[52] U.S. Cl. .............. 436/518; 356/445; 385/12; 385/36; 385/129; 385/130; 422/55; 422/58; 422/82.05; 422/82.11; 435/7.5; 435/287.1; 435/287.2; 435/287.9; 435/288.7; 435/808; 436/164; 436/165; 436/525; 436/527; 436/532; 436/805

[58] Field of Search .............. 356/445; 385/12, 385/36, 129, 130; 422/55, 58, 82.05, 82.11; 435/287.1, 287.2, 288.7, 808, 7.5, 287.9; 436/518, 525, 527, 532, 164, 165, 805

[56] References Cited

U.S. PATENT DOCUMENTS

| 4,844,613 | 7/1989 | Batchelder et al. | 356/318 |
| 4,877,747 | 10/1989 | Stewart | 436/525 |
| 5,242,828 | 9/1993 | Bergstrom et al. | 435/808 |
| 5,341,215 | 8/1994 | Seher | 356/445 |
| 5,374,563 | 12/1994 | Maule | 436/165 |
| 5,436,161 | 7/1995 | Bergstrom et al. | 435/291 |

FOREIGN PATENT DOCUMENTS 0 305 109 A1  1/1989  European Pat. Off.  ........ G01N 21/55

OTHER PUBLICATIONS

Jordan, et al., "Characterization of Poly-L-lysine Adsorption onto Alkanethiol-Modified Gold Surfaces with Polarization-Modulation Fourier Transform Infrared Spectroscopy and Surface Plasmon Resonance Measurements", Dept. of Chemistry, UWM, Langmuir 1994, pp. 3642-43648.

*Primary Examiner*—Christopher L. Chin
*Attorney, Agent, or Firm*—Quarles & Brady

[57] ABSTRACT

A biosensor for use in a surface plasmon resonance (SPR) System includes a transparent substrate layer, a thin metallic film on the substrate, and an ultrathin organic layer of a material which is polyanionic and adsorbs on the metallic film, and a layer of polylysine on this polyanionic material. In one embodiment, there is an outer layer on the polylysine which binds with a specific desired analyte.

10 Claims, 2 Drawing Sheets

ANALYTICAL BIOSENSOR

This invention was made with United States government support awarded by NSF GRANT # CHE 9302850. The United States Government has certain rights in this invention.

FIELD OF THE INVENTION

This invention relates to biosensors for use in biological, biochemical and chemical testing. More particularly, it relates to biosensors for the detection of analytes using surface plasmon resonance.

BACKGROUND OF THE INVENTION

Surface plasmon resonance (SPR) is a surface optical technique which is sensitive to the thickness and index of refraction of material at the interface between a noble metal (e.g. gold, silver, or copper) and a bulk medium, such as air or water. Surface plasmon resonance may be achieved by using the evanescent wave which is generated when a laser beam linearly polarized parallel to the plane of incidence (p-polarized) impinges onto a prism coated with a thin metal film. The metal may also be coated onto a thin transparent substrate such as glass, and this glass brought into optical contact with the prism. SPR is most easily observed as a reduction of the totally internally reflected light just past the critical angle of the prism. This angle of minimum reflectivity (denoted as the SPR angle) shifts to higher angles as material is adsorbed onto the metal layer. The shift in the angle can be converted to a measure of the thickness of the adsorbed or added material by using complex Fresnel calculations and can be used to detect the presence or absence of materials on top of the metal layer.

In using SPR to test for biological, biochemical or chemical substances, a beam of light from a laser source is directed through a prism onto a biosensor consisting of a transparent substrate, usually glass, which has one external surface covered with a thin film of a noble metal, which in turn is covered with an organic film that interacts strongly with an analyte, such as a biological, biochemical or chemical substance. The organic film can contain substances, such as antibodies or antigens, which can bind with an analyte in a sample to cause an increased thickness which will shift the SPR angle. By either monitoring the postition of the SPR angle, or the reflectivity at a fixed angle near the SPR angle, the presence or absence of an analyte in the sample can be detected.

Various types of equipment for using SPR with a biosensor for biological or biochemical or chemical substances are disclosed in the Liedberg, et al. article in Sensors and Actuators, Vol. 4, 1983, page 299; European Patent Application 0305108; and, the recently issued Maule U.S. Pat. No. 5,374,563.

The use of SPR as a testing tool offers several advantages; it is fast, it requires no labeling and it can be done on site. However, to fully achieve these advantages there is a need for a simple, practical biosensor which can be readily modified or adapted to test for a wide variety of analytes, including, biological, biochemical or chemical substances.

SUMMARY OF THE INVENTION

It is the object of the present invention to disclose an improved biosensor for use with SPR to test for the presence of an analyte.

The improved biosensor of the present invention comprises (i) a transparent substrate, (ii) a thin film of metal on one external surface of the transparent substrate, and (iii) an ultrathin organic film that is comprised of a layer of polyanionic material which is terminated by negatively charged functional groups to create a polyanionic surface that binds to the metal, and a layer of polycationic polylysine (poly-L-lysine) bonded to the polyanionic material. To provide a selective and specific sensor, the analyte binding can occur to the polylysine surface, to a chemically modified polylysine surface, or to an outer layer bound to the polylysine surface. An example of modified polylysine could include biotinylated PL; and an example of an outer layer may comprise an antibody or antigen.

DESCRIPTION OF THE PREFERRED EMBODIMENT

Figure 1:
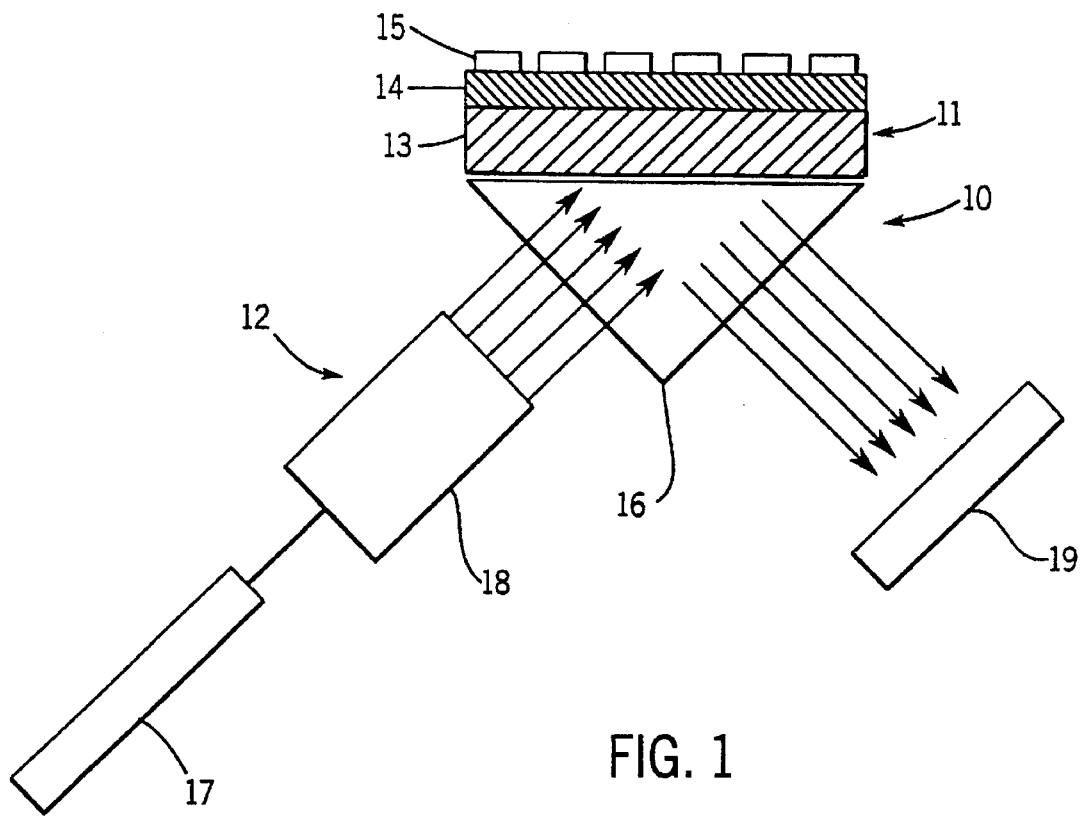
FIG. 1 is a schematic view of the preferred embodiment of the SPR biosensor of the present invention.
Figure 2:
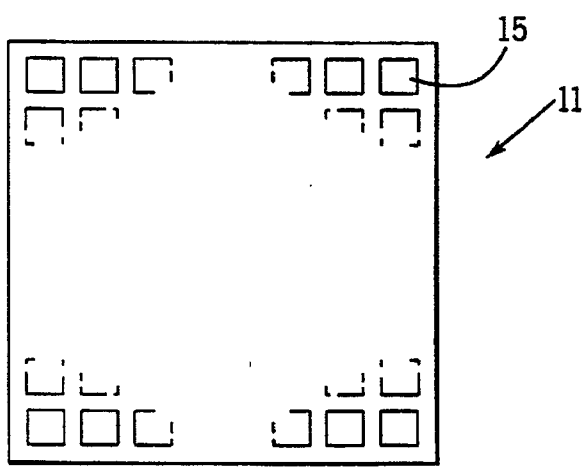
FIG. 2 is a top elevational view of the biosensor showing the multiple elements for analyte detection.
Figure 3:
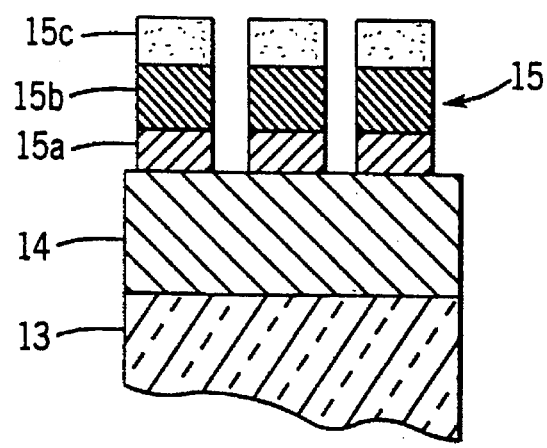
FIG. 3 is a partial cross-sectional view of the biosensor.

In the preferred embodiment of the invention seen in FIGS. 1-3, the SPR biosensor system 10 consists of a biosensor 11 and SPR optical readout components, generally referred to as 12. The biosensor 11 comprises a glass substrate 13, a thin noble metal film 14 on the surface of the substrate 13, and a photopatterned ultrathin organic film 15 on the metal surface. This biosensor 11 is coupled to a glass prism 16 with the aid of an index matching fluid (not shown). The SPR readout is accomplished with a monochromatic light source 17, such as a laser, a beam expander or any focusing or collimating optics 18, and a light sensitive detector 19.

FIG. 2 shows a top view of the preferred embodiment of the biosensor 11 illustrating its multi-element nature. The ultrathin organic film 15 has been patterned (e.g. photopatterned) on the noble metal surface 14 into an array of islands. Each island may comprise a slightly different organic film for the improved detection of a single analyte or the detection of multiple analytes using a single biosensor 11. Alternatively, the biosensor 11 may comprise a set of uniform coatings (rather than islands) of metal 14 and organic film 15; thereby only allowing for the detection of a single analyte.

FIG. 3 presents a partial cross-sectional view of the photopatterned biosensor 11. The glass substrate 13 has a thin metal coating 14 and adsorbed to the metal surface is the ultrathin organic film 15 which may be composed of several molecular layers 15a, 15b, and 15c. In the preferred embodiment of the present invention 15a is a material capable of adsorption onto the noble metal film 14 which creates a polyanionic surface (e.g. 11-mercaptoundecanoic acid (MUA) adsorbed onto a gold surface through the sulfhydryl group). The resulting polyanionic surface provides for the robust yet reversible electrostatic adsorption of the polycation polylysine (PL) 15b. The layer 15b also may comprise complexes of polylysine and other substances, such as a polynucleotide-polylysine complex or a receptor-polylysine complex. In the embodiment of FIG. 3, the polylysine monolayer 15b is covered with another layer 15c, which has the ability to bind selectively and with high affinity to a specific analyte (not shown).

Figure 4:
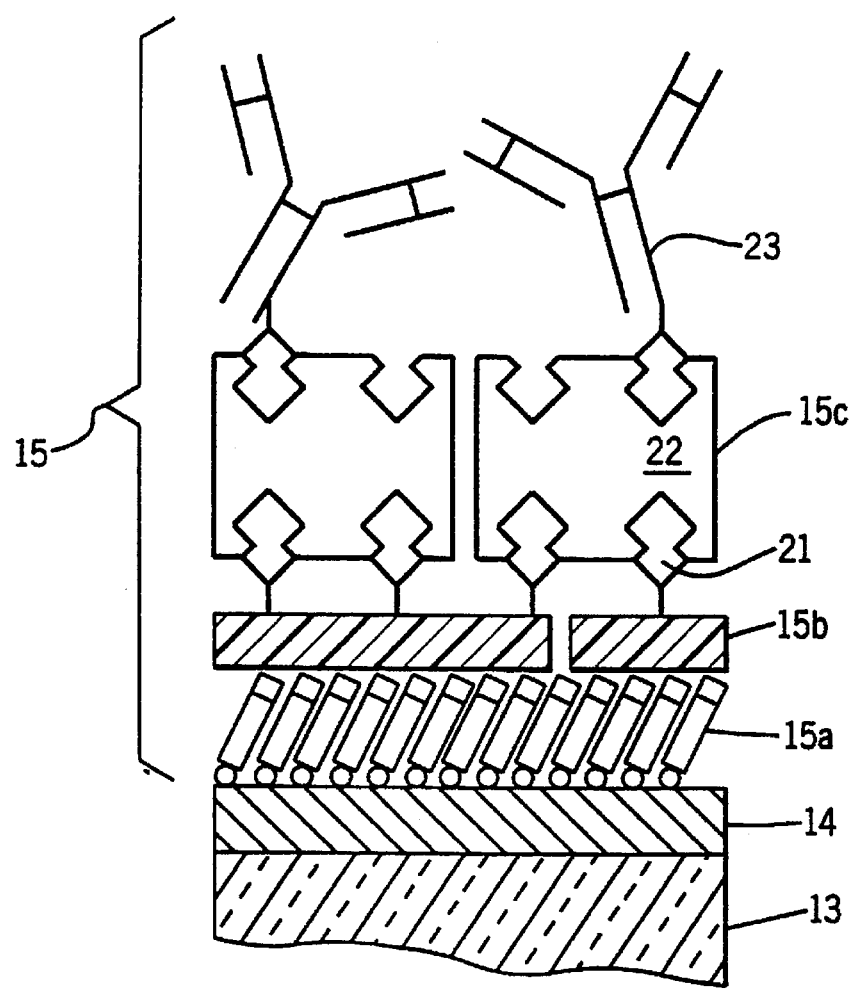
FIG. 4 is a schematic view showing the molecular components of the various layers of a biosensor of FIG. 3.

As seen schematically in FIG. 4, the layer 15c comprises a compound, such as biotin 21, which binds to the polylysine layer 15b and a substance, such as avidin 22, which binds to the biotin. If the analyte to be detected is an antigen (not shown), the outer layer 15c will also include a biotinylated antibody 23 which binds to the avidin and which can be used to selectively bind a specific antigen to the biosensor.

Using a fixed angle SPR system, the intensities of the reflected beam will differ for the islands which are bound to an analyte, such as an antigen, compared with the islands not bound to said analyte. Alternatively, the SPR system may monitor a range of angles in order to detect an analyte via a shift in the SPR angle. Finally, the intensities of any type of control which have a greater or lesser thickness than non-controls will be different than those of the non-controls. As a result, the biosensor can be used with an SPR system to detect the presence or absence of an analyte.

Polylysine (poly-L-lysine) was selected for use as the adsorbed polycationic material for a variety of reasons. The chemical structure and conformation of the polylysine are well characterized in bulk solution, and it exists in a random coil in its polycationic form in the pH range that the carboxyl groups of the MUA are deprotonated. In addition, it forms a flat, thin, monolayer on the MUA.

The polylysine is versatile. It binds with tumor cell markers in liquid samples. It can be modified either by reaction of the amine groups with various molecules or by the replacement of some lysine residues with other amino acids so that it may be coupled to antigens, immunoglobulins, receptors, or nucleic acids to form the functional basis of an immunological sensor or a sensor of specific nucleic acid fragments. The immunological sensor is able to detect epitopes on viruses, bacteria, toxins, environmental pollutants, or transformed cells. The nucleic acid sensor is able to detect specific polynucleotide sequences in solution making it useful for viral or bacterial identification, for HLA typing, and for DNA sequencing.

The polylysine preferred for use in the invention is that having a chain length in the range of 30 to 500 lysyl residues and a molecular weight of about 3900 to about 65,000.

When the biosensor 11 is to be used to detect substances that do not bond selectively or with high affinity to the polylysine, the PL can be modified (e.g. biotinylated), as demonstrated in the Examples. In place of biotin, any other compound that binds both to polylysine and a linking compound, such as avidin, also can be used. Linking compounds other than avidin and biotin, also might be used. Other linking compounds that can be used for some applications are diethylene triamine pentaacetic acid. dianhydride (DTPA) or 1-Ethyl-3-(3-Dimethylaminopropyl) carbodiimide Hydrochloride (EDC).

Although the use of 11-mercaptoundecanoic acid (MUA) is preferred for the formation of the polyanionic surface 15a, any other substance that forms a suitable flat, thin, polyanionic monolayer on the metal film 14 and which binds with polylysine 15b also can be used.

As seen in FIG. 4, the MUA layer 15a consists of molecules which are oriented nearly perpendicularly to the surface of the metal layer 14. The monolayer of PL 15b is adsorbed with its backbone aligned parallel to the gold (Au) surface. The outer layer 15c consists of the biotin bound to the polylysine layer and to avidin which is in turn bound to biotinylated antibody.

Photopatterning of the thin organic layer 15 may be achieved by photoinduced desorption of the alkanethiol monolayer 15a from the metal surface. This photoinduced desorption can be accomplished before or after the adsorption of the PL 15b and outer layer 15c. Additionally, the surface may be photopatterned through the use of photolabile functional groups attached to the PL monolayer 15c.

The Glass-Au-MUA-PL based biosensor is preferred because it may be readily reused simply by washing the coated surface in an aqueous solution at pH >12 or <4. The remaining Glass-Au-MUA combination can then be reconstituted by recharging with a new polylysine layer.

The present invention is illustrated by the following examples:

EXAMPLE 1

A flat 47 nm gold film is vapor deposited at room temperature onto 18 mm×18 mm square glass microscope slide covers using the procedure described by Barner B. J.; Corn R. M., Langmuir 1990, 6, p. 1023. They are annealed at about 300° Centigrade for one hour. An 11-mercaptoundecanoic acid (MUA) flat monolayer (17 Angstroms thick) is self-assembled onto the gold film from a 1 mM ethanolic solution by exposing it to the solution for at least 18 hr. followed by rinsing with ethanol.

EXAMPLE 2

A slide of Example 1 with its gold and MUA layers is dipped into a buffered (5 mM $NaHCO_3$, pH 8.5) aqueous solution of 0.2 mg/ml polylysine hydrobromide (average molecular weight 14000) to adsorb a flat monolayer of the polylysine (10.5 Angstroms thick) onto the MUA monolayer.

EXAMPLE 3

A slide from Example 2 with its gold film, MUA monolayer and polylysine monolayer is photopatterned to form 500 µm polylysine islands using a mask and ultraviolet light from a 200 Watt mercury arc lamp for a 2 hour exposure time. The slide is rinsed with water and ethanol to remove the MUA and PL from the unmasked areas and obtain a slide with islands of MUA and polylysine layers. The slide is then dipped into an aqueous preparation containing tumor cell markers.

EXAMPLE 4

Using a slide from Example 3 and an SPR system of the type seen in FIG. 1, a p-polarized light beam from a HeNe laser (632.8 nm) is impinged upon a triangular prism. The reflectivity of the laser-light is monitored at a fixed angle of incidence and the change in reflectivity is recorded. The difference between the reflectivity of the gold, MUA, polylysine, tumor cell markers and the MUA, gold and polylysine islands is readily seen.

EXAMPLE 5

A slide from Example 1 with its gold and MUA layer is dipped into a buffered (5 mM $NaHCO_3$, pH 8.5) aqueous solution containing 0.1 mg/ml of the biotinylated polylysine which has been prepared by reacting 15% of the lysine residues of the polylysine with an N-hydroxy succinimide ester of biotin. The thickness of the biotinylated polylysine layer is about 14 Angstroms.

EXAMPLE 6

A slide from Example 5 is exposed to a buffered solution (5 mM $NaHCO_3$ pH 8.5) of 0.03 mg/ml avidin to form a layer of avidin about 42 Angstroms thick upon the biotinylated polylysine layer.

EXAMPLE 7

A slide from Example 6 is treated with a biotinylated antibody such as goat anti-human IgA+IgG+IgM. The resulting biosensor has the structure displayed schematically in FIG. 4. The slide is then photopatterned as described in Example 3 to form gold-MUA-biotinylated PL-Avidin-biotinylated antibody islands. The slide with the biotinylated antibody is then exposed to an antigen, human gamma globulin, containing medium for 5 minutes. The SPR procedure of Example 4 is repeated and it is found that because of differences in reflectivity the islands to which the antigen has been attached can be readily distinguished from control areas and control islands.

It will be apparent to those skilled in the art that a number of changes and modifications can be made without departing from the spirit and scope of the present invention.

It also will be apparent that the biosensor of the present invention may be used to test for a wide variety of analytes, such as volatile substances in the air or other gases, or dissolved or suspended substances in a wide variety of liquids, including body fluids and water. Therefore, it is intended that the invention be limited only by the claims.

We claim:

1. An improved surface plasmon resonance (SPR) biosensor for use in a system for detecting an analyte, which system comprises a biosensor, a prism, a source of light for directing a beam of light through the prism upon said biosensor and a light detector, said biosensor comprising a transparent substrate, a metallic film on said substrate, an ultrathin organic layer comprised of a polyanionic material having terminal functional groups adsorbed upon said metallic film, a layer of polycationic polylysine bound to said polyanionic layer and an outer layer bound to the polylysine layer, said outer layer having the ability to specifically bind to the polylysine and the analyte to be detected.

2. A biosensor of claim 1 in which the polyanionic material is an alkanethiol compound.

3. A biosensor of claim 1 in which the polyanionic material is 11-mercaptoundecanoic acid.

4. A biosensor of claim 1 in which the metallic film is gold.

5. A biosensor of claim 1 in which the transparent substrate is glass.

6. A biosensor of claim 1 in which the outer layer forms a plurality of islands.

7. A biosensor of claim 6 in which the outer layer comprises a polynucleotide-polylysine complex.

8. A biosensor of claim 6 in which the outer layer comprises a receptor-polylysine complex.

9. A biosensor of claim 1 in which the outer layer contains avidin which is bound to the polylysine by biotin.

10. A biosensor of claim 9 in which the outer layer comprises a biotinylated antibody bound to the avidin.

* * * * *